United States Patent [19]

Butler et al.

[11] Patent Number: 5,167,624
[45] Date of Patent: Dec. 1, 1992

[54] EMBOLUS DELIVERY SYSTEM AND METHOD

[75] Inventors: James R. Butler, Ingleside, Ill.; William C. McCoy, Zionsville, Ind.

[73] Assignee: Catheter Research, Inc., Indianapolis, Ind.

[21] Appl. No.: 612,076

[22] Filed: Nov. 9, 1990

[51] Int. Cl.⁵ .............................................. A61B 17/12
[52] U.S. Cl. ..................................... 604/60; 606/191; 606/198
[58] Field of Search ............... 606/200, 195, 198, 151, 606/108, 191; 128/831, 843; 604/104, 60

[56] References Cited

U.S. PATENT DOCUMENTS

| | | |
|---|---|---|
| 1,694,246 | 12/1928 | Boyne . |
| 2,269,963 | 1/1942 | Wappler . |
| 3,833,003 | 9/1974 | Taricco . |
| 4,282,875 | 8/1981 | Serbinenko et al. . |
| 4,445,896 | 5/1984 | Gianturco . |
| 4,471,779 | 9/1984 | Antoshkiw et al. . |
| 4,494,531 | 1/1985 | Gianturco . |
| 4,512,342 | 4/1985 | Zaneveld et al. . |
| 4,543,090 | 9/1985 | McCoy . |
| 4,545,367 | 10/1985 | Tucci . |
| 4,601,705 | 7/1986 | McCoy . |
| 4,655,746 | 4/1987 | Daniels et al. . |
| 4,662,885 | 5/1987 | DiPisa, Jr. . |
| 4,686,962 | 8/1987 | Haber . |
| 4,688,553 | 8/1987 | Metals . |
| 4,708,718 | 11/1987 | Daniels . |
| 4,732,152 | 3/1988 | Wallsten et al. . |
| 4,739,768 | 4/1988 | Engelson . |
| 4,744,364 | 5/1988 | Kensey . |
| 4,758,222 | 7/1988 | McCoy . |
| 4,800,882 | 1/1989 | Gianturco . |
| 4,813,934 | 3/1989 | Engelson et al. . |
| 4,832,047 | 5/1989 | Sepetka et al. . |
| 4,884,579 | 12/1989 | Engelson . |
| 4,944,727 | 7/1990 | McCoy . |
| 4,994,069 | 2/1991 | Ritchart et al. . |
| 5,040,548 | 8/1991 | Yock ............................... 606/194 X |

FOREIGN PATENT DOCUMENTS 223065 6/1985 Fed. Rep. of Germany .

OTHER PUBLICATIONS

Perry, Stanton B. et al., "Coil Embolization to Occlude Aortopulmonary Collateral Vessels and Shunts in Patients with Congenital Heart Disease", J. Am. Coll. Cardiol., vol. 13, Jan. 1989, pp. 100–108.
Hawkins, Jeffrey et al., "Retrievable Gianturco-Coil Introducer", Radiology, vol. 158, Jan. 1986, pp. 262–264.
Fuhrman, Bradley, P. et al., "Coil Embolization of Congenital Thoracic Vascular Anomalies in Infants and Children", Therapy and Prevention—Vascular Anomalies, vol. 70, No. 2, Aug. 1984, pp. 285–289.
Berkman, William A. et al., "Varicoceles: A Coaxial Coil Occlusion System", Radiology, vol. 161, No. 1, Apr. 1984, pp. 73–77.
Ralston, Matthew D. et al., "Evaluation of Embolization Distal to Arterial Occlusion by Transcatheter Electrocoagulation (TCEC) and Gianturco Coils", Investigative Radiology, vol. 18, Mar.–Apr. 1983, pp. 171–176.
Chuang, Vincent P. et al., "Complications of Coil Embolization: Prevention and Management", AJR 137, Oct. 1981, pp. 809–813.
Szarnicki, Robert et al., "Wire Coil Embolization of (List continued on next page.)

Primary Examiner—Michael H. Thaler
Attorney, Agent, or Firm—Barnes & Thornburg

[57] ABSTRACT

A method and apparatus are provided for passing an embolus into and through the lumen of a catheter to reach a destination in a blood vessel or the like. Once the embolus emerges from the catheter, it lodges in place at the destination in the blood vessel to allow formation of a vessel-occluding blood clot around the embolus.

30 Claims, 2 Drawing Sheets

OTHER PUBLICATIONS

Systemic-Pulmonary Artery Collaterals Following Surgical Correction of Pulmonary Artresia", J. Thorac. Cardiovasc. Surg., vol. 81, No. 1, Jan. 1981, pp. 124–126.

Gianturco, C. et al., "Mechanical Devices for Arterial Occlusion", vol. 124, No. 3, Jul. 1975, pp. 428–435.

Anderson, James H. et al., "'Mini' Gianturco Stainless Steel Coils for Transcatheter Vascular Occlusion", Diagnostic Radiology, vol. 132, Aug. 1979, pp. 301–303.

Chuang, Vincent P. et al., "A New Improved Coil for Tapered-Tip Catheter for Arterial Occlusion", Radiology, vol. 135, May 1980, pp. 507–509.

Thompson, James N. et al., "Embolization Techniques in Vascular Tumors of the Head and Neck", Head & Neck Surgery, vol. 2, Sep.–Oct. 1979, pp.25–34.

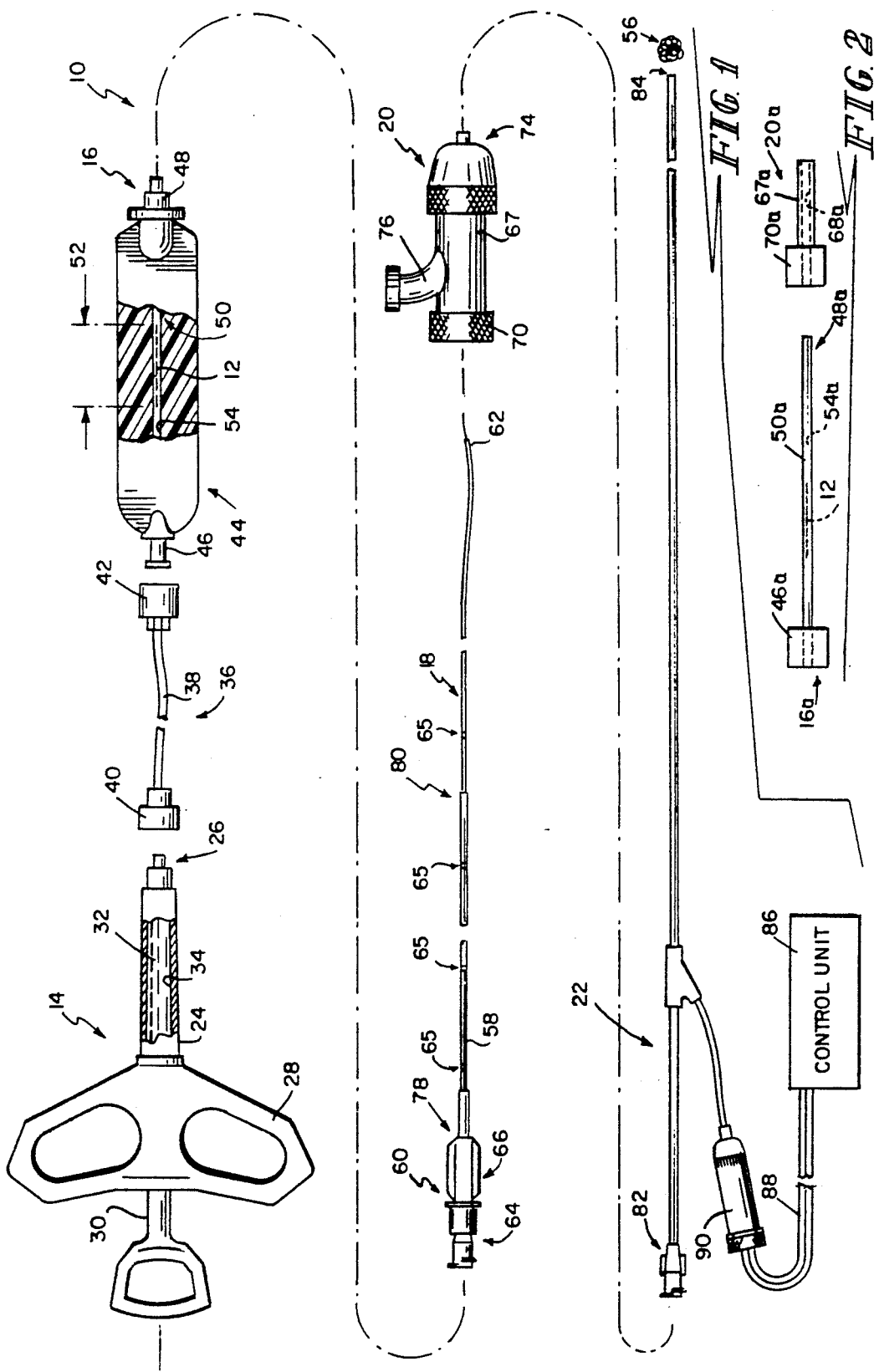

EMBOLUS DELIVERY SYSTEM AND METHOD

BACKGROUND AND SUMMARY OF THE INVENTION

This invention relates to a vessel occlusion system, and particularly to a system for delivering an embolus through a catheter or the like into a vessel situated in a body to occlude or close the vessel. More particularly, this invention relates to a method and apparatus for moving an embolus through an introducer catheter inserted through a venotomy into a body to reach a destination in a blood vessel or the like and occlude the vessel during a surgical procedure.

Embolization is a procedure used by surgeons to block fluid flow through a blood vessel or organ. Typically, a mass of material called an embolus is inserted into a body using a catheter and lodged in a blood vessel or organ to provide an obstruction therein. Lodging an embolus in a blood vessel obstructs blood flow through the vessel and causes a thrombus or blood clot to develop in the vessel. The thrombus remains attached to the embolus and blood vessel wall at its place of origin to plug the vessel and obstruct blood or other fluid flow therethrough.

Embolization is used, for example, for therapeutic purposes to reduce blood loss during hemorrhage or treatment of unresectable lesions or to permit preoperative control of blood flow. Embolization of feeding vessels is known to reduce bleeding during surgery. For example, it is used in surgery prior to resection of vascular tumors.

Many types of emboli are known. For example, coils made of spring wire, sponges made of absorbable gelatin or other chemical cross-linking means such as cyanoacrylate or the like, detachable balloons, umbrella-like devices, and other types of plugs are used to embolize a vessel. Any device which has thrombotic properties when placed in a vessel having a proper internal diameter and does not cause significant foreign body reaction can be used to embolize a vessel to occlude the vessel totally or partially.

A guide wire can be used to load an embolus into an introducer catheter or to discharge an embolus from its place in an introducer catheter into a vessel or both. A guide wire sized to pass through the lumen of the introducer catheter can be used to move an embolus into and out of an introducer catheter as long as the surgeon has the necessary skill and expertise.

One object of the present invention is to provide a method of hydraulically delivering a vessel-occluding embolus into and through a catheter to each blood vessel branching out from a trunk-like vein during a surgical procedure.

According to the present invention, a method is provided of passing an embolus into and through the lumen of a catheter to reach a destination outside of the catheter in a vessel. Initially, the catheter is inserted through a venotomy into a body and guided therein to aim the outlet of the catheter into the selected vessel. An embolus is positioned outside of the catheter in a hollow cartridge coupled to the lumen of the catheter at its inlet. A stream of pressurized fluid is then conducted through the hollow cartridge to discharge the embolus from the cartridge into the lumen of the catheter and propel the embolus through the lumen so that the embolus exits at the outlet of the catheter and reaches the destination in the vessel. The fluid used to flush the embolus into and through the catheter is water or another biologically compatible fluid such as saline.

In preferred embodiments, the positioning step includes the steps of providing a hollow cartridge formed to include a passageway therein containing the embolus and coupling the hollow cartridge to the catheter at the inlet to place the passageway and the lumen in communication to permit movement of the embolus therebetween through the inlet of the catheter. The conducting step further includes the steps of providing a supply of fluid and pressurizing a predetermined volume of fluid from the supply at a predetermined rate to generate the stream of pressurized fluid. For example, it has been observed that only 0.5-3 cubic centimeters of fluid are needed to deliver an embolus to a target site in a collateral blood vessel using the method of the present invention.

The embolus is preferably a normally coiled spring that has been straightened to a somewhat linear shape to assume an "uncoiled" configuration for containment in the cylindrical passageway formed in the cartridge. The tendency for the uncoiled spring to reconfigure itself to its coiled configuration causes the spring (embolus) to exert a predetermined force against an interior wall defining the passageway to retain the spring (embolus) temporarily in an initial position within the cartridge passageway. Advantageously, the stream of pressurized fluid is used to apply a predetermined amount of work to the embolus to overcome frictional forces between the embolus and the interior wall of the cartridge passageway to dislodge the embolus from its place in the hollow cartridge so that it can be moved by the stream of pressurized fluid into and through the catheter to reach its destination in the vessel.

Illustratively, the catheter used to deliver the embolus to the target site is guided through various body passageways to reach the target site by means of a second catheter having a lumen sized to receive the embolus-delivery catheter therein. The second catheter is preferably steerable and aimable by remote control to guide the embolus-delivery catheter extending therethrough to the mouth of the selected blood vessel or organ containing the target site.

Advantageously, the method and apparatus of the present invention permit a surgeon to embolize one or more vessels or organs in a body without using a guide wire to push an embolus into or through an embolus-delivery catheter to reach the target site in the body. An embolus-delivery catheter is sometimes called an "introducer" catheter. Further, use of a stream of pressurized fluid to move am embolus from a hollow cartridge into and through an introducer catheter provides an embolus delivery system that is easily manageable by the surgeon during embolization. Such a hydraulic system offers many advantages in use because it operates to cause a uniform, predetermined force to be applied to an embolus on command during each embolization.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is an exploded, unassembled side elevation view of an embolus delivery system in accordance with the present invention showing a syringe means, a hollow cartridge assembly containing a packed coil embolus therein, an introducer catheter, a catheter clamp assembly, a steerable and aimable catheter, and a reformed coil embolus after it has emerged from the introducer catheter;

FIG. 2 is a diagrammatic view of another embodiment of a hollow cartridge assembly suitable for use in the embolus delivery system shown in FIG. 1;

DETAILED DESCRIPTION OF THE DRAWINGS

Figure 3:
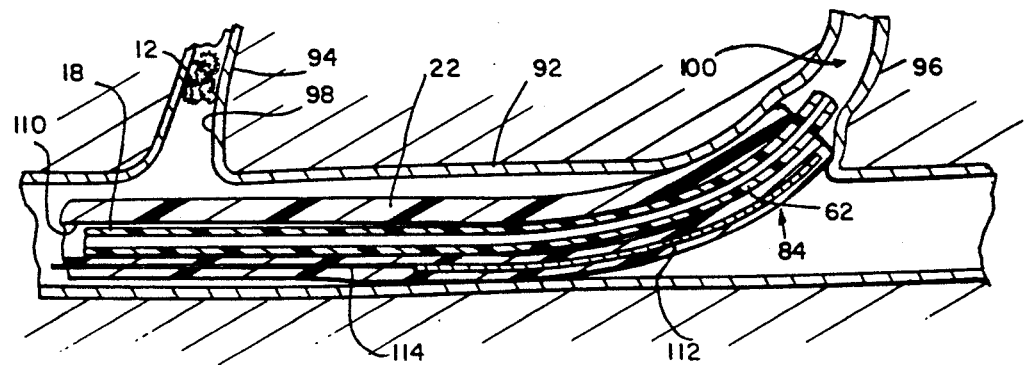
FIG. 3 is a sectional view of the distal end of the system of FIG. 1 in place in a main body vessel (e.g., vein or artery) showing how the introducer catheter is aimed into a collateral vessel selected to be occluded prior to delivery of an embolus through the introducer catheter to the target site in the selected collateral vessel and also showing another collateral vessel previously plugged by a reformed coil embolus.

During vascular surgery, surgeons find it necessary to occlude or ligate certain veins, arteries, or collateral blood vessels to control blood flow through the body undergoing an operation. Of course, it is also desirable to occlude body organs other than blood vessels, and therefore, the present invention is not intended to be limited to occlusion of veins, arteries, or vessels. For illustrative purposes, the invention is described in an application for delivering a coil embolus to a vessel.

The improved method and apparatus of the present invention is well suited for delivering coil emboli to a vessel in a simple, efficient, repeatable, and predictable manner. Means is provided for inserting an embolus into an introducer catheter quickly and easily and also discharging the embolus from the introducer catheter into a selected vessel in a body without using a guide wire.

A system 10 for transcatheter embolization of selected vessels or organs in a body is illustrated in FIG. 1. Advantageously, this system 10 is well-suited for delivering a coil embolus 12 (or other embolus) to a target site in a body vessel or organ. Once it reaches the target site, the coil embolus 12 partially occludes the vessel and causes a blood clot to form around the coil embolus 12 at the target site. Later, scar tissue develops around the blood clot to occlude the vessel or organ totally. It will be appreciated that the system 10 could be used to deliver various emboli other than coil emboli 12.

Embolus-delivery system 10 includes a syringe means 14, an embolus-dispensing cartridge 16, an introducer catheter 18, a catheter clamp assembly 20, and a steerable and aimable end-hole catheter 22. The syringe means 14 is used to deliver a stream of pressurized fluid to cartridge 16 and introducer catheter 18 to move an embolus out of its home in the cartridge 16 and into and through introducer catheter 18 toward its destination outside of the introducer catheter 18 in a blood vessel or the like. System 10 renders obsolete any need to use a guide wire (not shown) or other instrument to load an embolus into an introducer catheter to discharge an embolus from an introducer catheter.

In the illustrated embodiment, syringe means 14 includes a hollow barrel 24 having a nozzle 26 at one end and a handle 28 at the other end. A plunger 30 is inserted into the handle end of the barrel 24 and is movable therein to pressurize a predetermined volume of fluid 32 contained in a reservoir 34 therein and discharge that fluid 32 from the hollow barrel 24 through the nozzle 26. A hose assembly 36 interconnects nozzle 26 and cartridge 16 to conduct a stream of pressurized fluid 32 discharged from the nozzle 26 into cartridge 16. Hose assembly 36 includes a tube 38 having connector fittings 40, 42 at opposite ends.

Various fluid pump means (not shown) could be connected to cartridge 16 and operated to inject a stream of pressurized fluid into the cartridge 16 sufficient to dislodge an embolus 12 disposed therein and discharge the embolus 12 into a downstream catheter such as introducer catheter 18. A suitable fluid pump means (not shown) includes a pump assembly connected to a fluid supply and means for controlling filling and unfilling of the pump assembly. The controlling means is operable to admit a predetermined volume or slug of fluid into the pump assembly from the fluid supply and discharge that slug of fluid into cartridge 16 at a predetermined rate to discharge embolus 12 from cartridge 16.

An illustrative embodiment of an embolus-dispensing cartridge 16 is shown in FIG. 1. Cartridge 16 includes a body 44 having an inlet fitting 46 at one end and an outlet fitting 48 at the other end. Desirably, fittings 46 and 48 are of standard size and shape so that they mate easily with other attachment fittings, such as bayonet-style fittings, typically used to connect medical hoses, catheters, adaptors, and the like. Cartridge 16 is formed to include a passageway or tube 50 extending therethrough beginning at the inlet fitting 46 and terminating at the outlet fitting 48. An alternative embodiment of cartridge 16 is shown diagrammatically as cartridge 16a in FIG. 2. Cartridge 16a includes a tube 50a having an inlet fitting 46a at one end and an outlet mouth 48a at the other end for connecting to introducer catheter (not shown in FIG. 2).

A frangible appendage could be provided on one or both of inlet and outlet fittings 46, 48 to provide means for visually determining whether cartridge 16 has been connected previously to hose assembly 36 or introducer catheter 18. The frangible appendage is configured to break whenever the cartridge 16 is connected to a syringe, hose, introducer catheter, etc. For example, one or more single-use, breakaway tabs or rings could be attached to either the inlet fitting 46, the outlet fitting 48, or both to provide the frangible appendage.

As shown in FIG. 1, an embolus 12 is deposited in the cartridge passageway 50 in, for example, a central region 52 so that it is ready to be discharged through outlet fitting 48 whenever it is "hit" by the slug of fluid 32 expelled from syringe means 14. In FIGS. 1 and 2, embolus 12 is represented by a dotted line segment to indicate that embolus 12 is initially packed into passageway 50 to load the cartridge 16. In the case of a coiled spring embolus 12, it is preferably unraveled to assume a somewhat straight shape and loaded into the passageway 50 during factory assembly of cartridge 16. Essentially, the coiled spring 12 is uncoiled or straightened to assume a packed position in the passageway 50 and configured to exert a light predetermined force against the interior wall 54 of the passageway 50 to retain the spring 12 in the cartridge 16 until a stream of pressurized fluid 32 is injected into passageway 50.

It will be appreciated that a variety of coiled spring emboli are available in the marketplace. Presently, a helical coil or curled segment made of small diameter platinum wire without any fiber tails or threads attached thereto is the preferred embolus to use in connection with embolus-delivery system 18. For example, suitable coil emboli are available from Target Therapeutics, Inc. of San Jose, Calif.

As shown in FIG. 1, a coiled spring embolus 12 can be uncoiled and straightened using suitable automated or manual means to permit loading into the cartridge passageway 50. Such an embolus 12 is retained temporarily in a fixed position in passageway 50 by frictional engagement of the coiled spring embolus 12 against the interior wall 54. The internal diameter of passageway 50 is matched to the size of embolus 12 to be retained therein to ensure that the straightened spring embolus 12 is unable to move to assume its original helical or coiled shape. However, injection of a stream of pressurized fluid into the inlet end 46 of passageway 50 at a sufficient rate will apply enough work to the spring 12 to overcome frictional forces between the spring 12 and the passageway wall 54, thereby dislodging the spring 12 and discharging it from cartridge 16 through outlet end 48. Once spring 12 emerges from the introducer catheter 18 at the target site in a vessel, it will coil or "reform" to assume a coiled shape similar to its original helical shape as shown at 56 in FIG. 1.

Introducer catheter 18 includes an outer sleeve or sheath 58 at its proximal end, a grip assembly 60 attached to the outer sleeve 58, and a distal tip 62 formed to include a mouth for discharging embolus 12 at the target site in a vessel. Grip assembly 60 includes a hub 64 configured to mate in a secure fluid-tight manner with outlet fitting 48 on cartridge 16 without obstructing travel of an embolus 12 from cartridge 16 into introducer catheter 18 and a handle 66 for use in manipulating introducer catheter 18.

One or more colored axially spaced bands 65 are provided on introducer catheter 18. These bands 65 can be used as markers or reference points to permit a user to determine the distance the introducer catheter 18 is projected into the lumen of the steerable and aimable catheter 22 during use of system 10.

Figure 6:
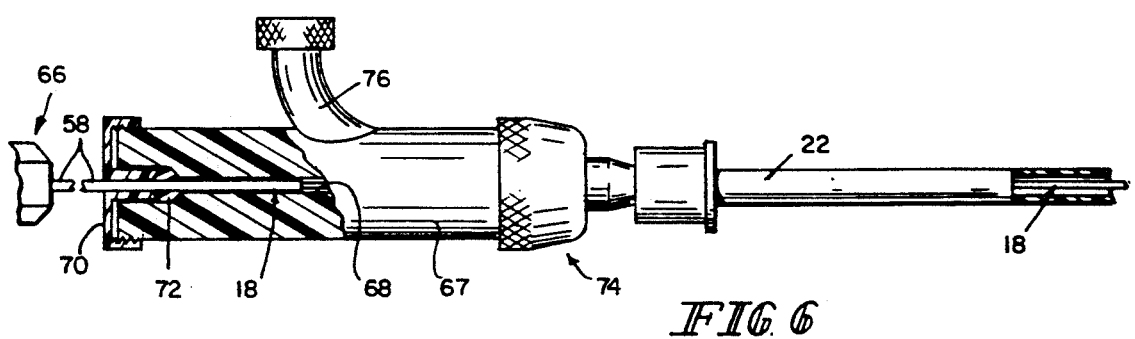
FIG. 6 is an enlarged view of the catheter clamp assembly of FIG. 1, as it clamps the introducer catheter in place in the lumen of the steerable and aimable catheter, showing the operation of the protective tubular sheath between the introducer catheter and the catheter clamp assembly to prevent deformation of the embolus-delivering passageway extending through the introducer catheter which might otherwise be caused by the clamping action of the clamp assembly on the introducer catheter.

A catheter clamp assembly 20 is used to lock the introducer catheter 18 in a selected axial position within the lumen of the steerable and aimable guide catheter 22. As shown in FIG. 6, clamp assembly 20 includes a body 67 formed to include a passageway 68 extending therethrough and having an internal diameter sized to permit sliding axial movement of the introducer catheter 18 in the passageway 68. A rotary clamp 70 (or any other suitable clamp means) and annular gasket 72 are mounted to the inlet end 72 of clamp assembly 20 to provide means for clamping an introducer catheter 18 extending through the passageway 68. An outlet fitting 74 is provided at the downstream end of body 67 to permit connection of clamp assembly 20 to guide catheter 22 while an introducer catheter 18 extends through body passageway 68 and into the lumen of guide catheter 22. A side branch flush tube 76 optionally is attached to a central portion of clamp body 67. An alternative embodiment of catheter clamp assembly 20 is shown diagrammatically as clamp assembly 20a in FIG. 2. Clamp assembly 20a includes a body 67a formed to include a passageway 68a extending therethrough and a clamp 70a at an upstream end for clamping an introducer catheter 18 extending through passageway 68a.

Figure 5:
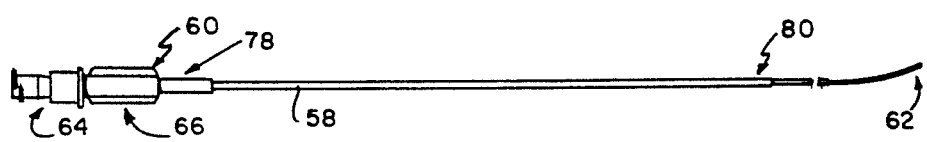
FIG. 5 is a side elevation view of an introducer catheter assembly according to the invention showing the protective tubular sheath at the proximal end of the introducer catheter.

Outer sleeve 58 is a tubular sheath that includes a lumen sized to receive introducer catheter 18 therein as shown best in FIGS. 5 and 6. The outer sleeve 58 includes an upstream end 78 connected to the proximal end of the introducer catheter 18, for example, inside the grip assembly 60 using suitable connection means. The outer sleeve 58 also includes a downstream end 80 extending a predetermined distance along the length of the introducer catheter 18 toward the distal tip 62 to ensure that the clamp 70 will engage and grip the hard outer sleeve 58 and not an unprotected section of the relatively soft introducer catheter 18 outside of the outer sleeve 58 when the introducer catheter 18 is fully inserted into the lumen of the guide catheter 22 and placed in a working position. Advantageously, the outer sleeve 58 is made of a hard, tough material such as polyvinyl chloride that will not deform under normal forces generated by tightening clamp 70 so that the clamp 70 will not compress the introducer catheter 18 and thereby block passage of embolus 12 through the lumen of the introducer catheter 18. Further, outer sleeve 58 minimizes kinking of the introducer catheter 18 and provides a clampable member having an enlarged diameter relative to the introducer catheter 18 that is easy to clamp without collapsing the introducer catheter 18. It will be appreciated that outer sleeve 58 could be formed as an integral part of introducer catheter 18.

Guide catheter 22 includes an inlet fitting 82 at its proximal end and an outlet opening 84 at its distal end as shown best in FIG. 1. Guide catheter 22 is illustratively a steerable and aimable catheter of the type available from Catheter Research, Inc. of Indianapolis, Ind. A control unit 86 is connected by wire harness 88 to a socket 90 provided on guide catheter 22. Control unit 86 provides remote control means to permit a surgeon to steer guide catheter 22 through body passages and aim the outlet opening 84 at selected targets within the body undergoing surgery.

Reference is hereby made to U.S. Pat. Nos. 4,543,090; 4,601,705; and 4,758,222 for descriptions of the structure, function, and operation of suitable steerable and aimable catheters. It will be appreciated that a variety of sizes, shapes, and kinds of guide catheters and guide wires could be used to guide introducer catheter 18 to its destination in a body and that, in certain circumstances, introducer catheter could be moved in a body to reach its target site without using any other catheter to guide it. It should also be understood that a steerable and aimable guide catheter could be used by itself to deliver an embolus to a destination in a body without using any separate introducer catheter.

Figure 4:
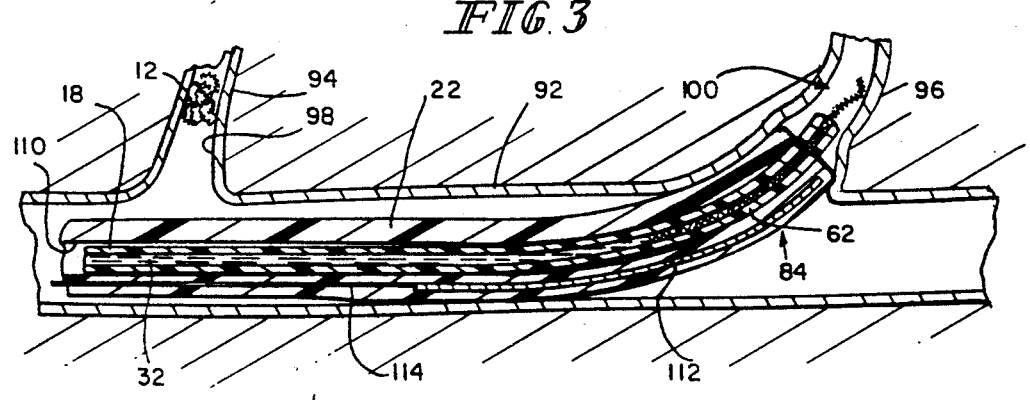
FIG. 4 is a view similar to FIG. 3 showing use of a stream of pressurized fluid to move a "straightened" coil embolus through the introducer catheter toward the target site in the selected collateral vessel.

Delivery of an embolus 12 to a target site in a blood vessel using embolus-delivery system 10 is illustrated in FIGS. 3 and 4. The distal end 84 of guide catheter 22 inserted through a venotomy into a body is advanced into a main blood vessel 92 having a pair of collateral blood vessels 94, 96 branching out from the main blood vessel 92. Collateral vessel 94 contains a coil embolus 12 that is wedged against the interior wall 98 of collateral vessel 94 to anchor the coil embolus in place so that blood begins to clot and form a vessel-occluding thrombus (not shown) around coil embolus 12. The guide catheter 22 is maneuvered using control unit 86 to aim the distal tip 62 of the introducer catheter 18 into the open mouth of the unoccluded collateral vessel 96 toward a target site 100 therein. The introducer catheter 18 must be inserted at least a couple of millimeters into the collateral vessel 96. Illustratively, a temperature-activated memory element 112 made of a shape-memory alloy is connected to a lead wire 114 and heated using control unit 86 to move the distal end of guide catheter 22 to assume the upwardly curved shape shown in FIGS. 3 and 4.

The introducer catheter 18 extends through the lumen 110 of guide catheter 22 and is movable axially therein until clamp 70 on the clamp assembly 20 is tightened to grip the outer sleeve 58 of introducer catheter 18 and prevent relative movement of introducer catheter 18 inside the lumen 110 of guide catheter 22. Once introducer catheter 18 has been maneuvered to reach the mouth of collateral vessel 96 and inserted therein as shown in FIG. 3, then clamp 70 can be loosened to permit the surgeon to push the introducer catheter 18 forward so that its distal tip 62 extends further into the collateral vessel 96 and faces target site 100. At this point, the introducer catheter 18 is locked by tightening the clamp 70 to prevent movement of introducer catheter 18 relative to guide catheter 22.

Desirably, the inner diameter of lumen 110 in guide catheter 22 is large enough to contain an angioscope (not shown) in addition to the introducer catheter 18. The angioscope can be used to permit the surgeon to view the interior regions of the main and collateral blood vessels as the guide catheter is steered to reach the collateral vessel 96 sought to be occluded. Once the surgeon is satisfied that the introducer catheter 18 is in collateral vessel 96 or aimed properly at the target site 100 in the collateral vessel 96 as shown in FIG. 3, the surgeon is free to use syringe means 14 to inject a slug of fluid into the cartridge 16 at a rate sufficient to dislodge the embolus 12 from its fixed position in the cartridge passageway 50 and propel the embolus 12 into and through the lumen of the introducer catheter 18. Preferably, the pressure generated by the syringe means 14 is about 200 to 300 psi.

The coil embolus 12 remains in a somewhat uncoiled and straightened packed shape as it travels through the lumen of the introducer catheter 18 and reforms to its helical coiled shape as soon as it emerges from the distal tip 62 of the introducer catheter 18. Using this technique, a coil emboli can be delivered to a target site 100 in collateral vessel 96 using biocompatible saline or the like without resort to use of a guide wire to move a coil embolus 12 either into or through an introducer catheter 18.

Although the invention has been described and defined in detail with reference to certain preferred embodiments, variations and modifications exist within the scope and spirit of the invention as described and defined in the following claims.

We claim:

1. A method of passing an embolus into and through the lumen of a catheter to reach a destination outside of the catheter, the method comprising the steps of
   providing a catheter formed to include an inlet end, an outlet end, and a lumen connecting the inlet to the outlet,
   positioning an embolus outside of the catheter in a hollow cartridge coupled to the lumen of the catheter at the inlet end, and
   conducting a stream of pressurized fluid through the hollow cartridge to discharge the embolus from the cartridge into the lumen of the catheter through said inlet end and propel the embolus through the lumen so that the embolus exits at the outlet of the catheter and reaches the destination outside of the catheter.

2. The method of claim 1, wherein the positioning step includes the steps of providing a hollow cartridge formed to include a passageway therein containing the embolus and coupling the hollow cartridge to the catheter at the inlet end to place the passageway and the lumen in communication to permit movement of the embolus therebetween through the inlet end.

3. The method of claim 2, wherein the conducting step further includes the steps of providing a supply of fluid and pressurizing a predetermined volume of fluid from the supply to generate the stream of pressurized fluid.

4. The method of claim 1, wherein the positioning step includes the steps of providing a cartridge having a tube formed to include a passageway containing the embolus lodged therein in frictional engagement with the tube and clamping one end of the tube to the inlet end of the catheter to place the passageway and the lumen in communication and permit the embolus to move from the passageway into the lumen through said inlet end.

5. The method of claim 4, wherein the conducting step includes the steps of providing a supply of fluid and introducing a predetermined volume of fluid from the supply at a predetermined rate into the passageway formed in the cartridge through a mouth formed in an end of the tube opposite the clamped end to generate the stream of pressurized fluid, and using the stream of pressurized fluid to apply a predetermined amount of work to the embolus to overcome frictional forces between the embolus and the tube and dislodge the embolus during the introducing step.

6. The method of claim 1, wherein the conducting step includes the steps of providing a supply of fluid, pressurizing a predetermined volume of fluid from the supply to generate the stream of pressurized fluid, and aiming the stream of pressurized fluid at the embolus in the passageway to cause the embolus to move out of the passageway and into the lumen through said inlet end.

7. The method of claim 1, wherein the embolus is a coiled spring straightened to assume a packed position in the passageway and configured to exert a predetermined force against a wall defining the passageway to retain the embolus temporarily in an initial position within the passageway and the conducting step includes the steps of providing a stream of pressurized fluid and using the stream of pressurized fluid to apply a predetermined amount of work to the embolus to overcome frictional forces between the embolus and the wall defining the passageway and move the embolus out of the passageway from its initial position into the lumen through said inlet end.

8. The method of claim 1, wherein the positioning step further includes the steps of providing a spring having a coiled shape to serve as the embolus, uncoiling the spring to cause it to move to assume a straightened shape, and packing the spring of straightened shape into the passageway, which passageway is sized to block the spring from reforming to its coiled shape so that the spring is lodged temporarily in a fixed position in the passageway by frictional engagement of the spring and a wall defining the passageway, and the conducting step includes the steps of providing a supply of fluid, pressurizing a predetermined volume of fluid from the supply to generate the stream of pressurized fluid, and using the stream of pressurized fluid to apply a predetermined amount of work to the spring to overcome frictional forces between the spring and the wall of the passageway and propel the spring from its fixed position in the passageway through the inlet end and through the lumen of the catheter so that the spring exits the outlet end and reforms to assume its coiled shape in the vessel at the destination.

9. A method of delivering an embolus to a destination, the method comprising the steps of
inserting a catheter into a body, the catheter being formed to include an inlet end, an outlet end, and a lumen connecting the inlet end to the outlet end,
guiding the catheter through the body to aim the outlet end of the catheter toward the destination,
supporting an embolus outside of the lumen in an initial position communicating with the inlet end formed in the catheter,
providing a stream of pressurized fluid, and
using the stream of pressurized fluid to apply at least a predetermined amount of work to the embolus to move the embolus from its initial position outside of the lumen through the catheter inlet end, lumen, and outlet end to its destination.

10. The method of claim 9, wherein the using step includes the steps of aiming the stream of pressurized fluid at the embolus and conducting the embolus and the stream of pressurized fluid into the lumen through the inlet end formed in the catheter.

11. The method of claim 9, wherein the using step further includes the steps of providing a supply of fluid and pressurizing a predetermined volume of fluid from the supply to generate the stream of pressurized fluid.

12. The method of claim 9, wherein the supporting step includes the steps of providing a hollow cartridge formed to include a passageway containing the embolus lodged temporarily therein in frictional engagement with a wall defining the passageway and coupling the hollow cartridge to the catheter at the inlet end to connect the passageway to the lumen to permit the movement of the embolus therebetween through the inlet end, and the using step further includes the steps of providing a supply of fluid, pressurizing a predetermined volume of fluid from the supply to generate the stream of pressurized fluid, and aiming the stream of pressurized fluid to apply a predetermined amount of work to the embolus to overcome frictional forces between the embolus and the wall of the passageway and dislodge the embolus during the using step.

13. The method of claim 9, wherein the supporting step includes the steps of providing a hollow cartridge containing the embolus therein and connecting the cartridge to the inlet end of the catheter to support the embolus in its initial position outside of the lumen.

14. The method of claim 13, wherein the using step includes the step of introducing the stream of pressurized fluid into the hollow cartridge for a predetermined length of time through an inlet end port formed in the hollow cartridge to discharge the embolus from the hollow cartridge through an outlet end port formed in the hollow cartridge into the inlet of the catheter.

15. The method of claim 13, wherein the providing step includes the step of connecting a syringe means having a body filled with a predetermined volume of fluid to an inlet end port formed in the hollow cartridge and moving a plunger in the body to discharge a stream of pressurized fluid from the syringe means into the hollow cartridge through the inlet end port.

16. The method of claim 13, wherein the embolus is a coiled spring uncoiled to assume a straightened, packed position in the hollow cartridge and configured to exert a Predetermined force against an interior wall of the hollow cartridge to retain the embolus in an initial position within the hollow cartridge, and the providing step includes the steps of supplying a predetermined volume of liquid and pressurizing the predetermined volume of liquid to generate the stream of pressurized fluid and provide said predetermined amount of work needed to overcome frictional forces between the embolus and the interior wall of the hollow cartridge.

17. The method of claim 9, wherein the supporting step further includes the steps of providing a spring having a coiled shape to serve as the embolus, uncoiling the spring to cause it to move to assume a straightened shape, and packing the spring of straightened shape into the passageway, which passageway is sized to block the spring from reforming to its coiled shape so that the spring is lodged temporarily in a fixed position in the passageway by frictional engagement of the spring and a wall defining the passageway, and the using step includes the steps of providing a supply of fluid and pressurizing a predetermined volume of fluid from the supply to generate the stream of pressurized fluid and apply a predetermined amount of work to the spring to overcome frictional forces between the spring and the wall of the passageway and propel the spring from its fixed position in the passageway through the inlet end and the lumen of the catheter so that the spring exits the outlet end and reforms to assume its coiled shape in the vessel at the destination.

18. The method of claim 9, wherein the providing step includes the step of containing a predetermined volume of fluid in a container having an outlet port and displacing the fluid in the container to discharge a stream of pressurized fluid from the container through the outlet port.

19. The method of claim 18, wherein the using step includes the steps of aiming the stream of Pressurized fluid discharged through the outlet port of the container at the embolus and conducting the embolus and the stream of pressurized fluid into the lumen through the inlet end formed in the catheter so that at least the embolus moves through the lumen to reach the destination.

20. A method of delivering an embolus to a destination in a selected vessel, the method comprising the steps of
inserting a catheter into a body, the catheter being formed to include an inlet end, an outlet end, and a lumen connecting the inlet end to the outlet end,
guiding the catheter through the body to aim the outlet end of the catheter into the selected vessel,
providing an embolus outside of the catheter, providing a stream of pressurized fluid, and using the stream of pressurized fluid to propel the embolus into and through the lumen through said inlet end and out said outlet end to its destination in a selected vessel to occlude the vessel.

21. The method of claim 20, wherein the guiding step includes the step of inserting the catheter a distance into the selected vessel before beginning the using step.

22. A method of delivering an embolus to a selected place in a vessel, the method comprising the steps of inserting an outer catheter into a body, the outer catheter being formed to include a lumen having an inlet end and an outlet end, guiding the outer catheter through the body to aim the outlet end of the lumen into a passageway of a selected vessel, inserting an inner catheter into the lumen of the outer catheter, the inner catheter being formed to include an embolus-conducting lumen having an embolus-admitting inlet end and an embolus-discharging outlet end, moving the inner catheter in the lumen of the outer catheter to position the embolus-discharging outlet end at about the outlet end of the outer catheter so that an embolus discharged from the embolus-conducting lumen is inserted into the selected vessel, connecting a hollow cartridge containing an embolus to the embolus-admitting inlet end of the inner catheter, and using a fluid to flush the embolus out of the hollow cartridge and move the embolus into and through the embolus-conducting lumen through said embolus admitting and embolus discharging ends to reach the selected place in the vessel to occlude the vessel.

23. The method of claim 22, wherein the using step further includes the steps of providing a supply of fluid and pressurizing a predetermined volume of fluid from the supply to generate the stream of pressurized fluid.

24. The method of claim 22, wherein the guiding step includes the step of inserting the outer catheter a distance into the selected vessel before completion of the moving step so that the outlet of the outer catheter is positioned in the selected vessel before the outlet end of the inner catheter is extended into the selected vessel.

25. The method of claim 22, wherein the connecting step further includes the steps of providing a hollow cartridge formed to include a passageway containing the embolus lodged temporarily therein in frictional engagement with a wall defining the passageway and coupling the hollow cartridge to the catheter at the inlet end to connect the passageway to the lumen to permit the movement of the embolus therebetween through the inlet end, and the using step further includes the steps of providing a supply of fluid, pressurizing a predetermined volume of fluid from the supply to generate the stream of pressurized fluid, and aiming the stream of pressurized fluid to apply a predetermined amount of work to the embolus to overcome frictional forces between the embolus and the wall of the passageway and dislodge the embolus during the using step into the inlet end.

26. The method of claim 25, wherein the connecting step further includes the steps of providing a spring having a coiled shape to serve as the embolus, uncoiling the spring to cause it to move to assume a straightened shape, and packing the spring of straightened shape into the passageway, which passageway is sized to block the spring from reforming to its shape so that the spring is lodged temporarily in a fixed position in the passageway by frictional engagement of the spring and a wall defining the passageway, and the using step includes the steps of providing a supply of fluid, pressurizing a predetermined volume of fluid from the supply to generate the stream of pressurized fluid, and employing the stream of pressurized fluid to apply a predetermined amount of work to the spring to overcome frictional forces between the spring and the wall of the passageway and propel the spring from its fixed position in the passageway through the inlet end and the lumen of the catheter so that the spring exits the outlet end and reforms to assume its coiled shape in the vessel at the destination.

27. An embolus delivery system, comprising a catheter having a lumen, the lumen having a inlet end, a cartridge containing an embolus, the cartridge including means for coupling to the catheter to the inlet end of the lumen so that the embolus can pass from the cartridge through the inlet end and into the catheter, and means for introducing fluid into the cartridge to discharge the embolus from the cartridge into the lumen of the catheter through said inlet end.

28. The system of claim 27, wherein the introducing means includes means for storing a supply of fluid and means for pressurizing a volume of fluid contained in the storing means to generate a stream of pressurized fluid that travels into the cartridge to move the embolus out of the cartridge and into the inlet end of the lumen of the catheter.

29. The system of claim 28, wherein the cartridge is formed to include a passageway containing the embolus lodged therein in frictional engagement with a wall defining the passageway and the pressurizing means provides means for imparting at least a predetermined velocity to the stream of pressurized fluid to cause the fluid to move through the passageway at a rate sufficient to overcome frictional forces between the embolus and the wall, dislodge the embolus, and propel the embolus through the inlet end into and through the lumen of the catheter.

30. The system of claim 29, wherein the embolus is a coiled spring straightened to assume a packed position in the passageway and configured to exert a predetermined force against the wall defining the passageway to retain the embolus temporarily in an initial position within the passageway.

* * * * *